United States Patent [19]
Tamai et al.

[11] Patent Number: 5,479,256
[45] Date of Patent: Dec. 26, 1995

[54] TRANSIENT GRATING SPECTROSCOPY

[75] Inventors: Naoto Tamai, Kyoto; Takashi Ito, Joytel-saiin 604, 32, Sanzo-cho, Saiin, Ukyo-Ku, Kyoto-shi, Kyoto; Tsuyoshi Asahi; Hiroshi Masuhara, both of Osaka, all of Japan

[73] Assignees: Research Development Corp. of Japan, Tokyo; Takashi Ito, Kyoto, both of Japan

[21] Appl. No.: 149,555

[22] Filed: Nov. 9, 1993

[30] Foreign Application Priority Data

Dec. 4, 1992 [JP] Japan ................... 4-325747

[51] Int. Cl.$^6$ ................................................. G01B 9/02
[52] U.S. Cl. ................................ 356/346; 356/345
[58] Field of Search .................. 356/346, 345, 356/353, 361, 328, 432 T

[56] References Cited

PUBLICATIONS

Fayer, Michael D., "Picosecond Holographic Grating Generation of Ultrasonic Waves", IEEE Journal of Quantum Mechanics, vol. QE–22, No. 8, Aug. 1986, pp. 1437–1451.

Primary Examiner—Sam A. Turner
Attorney, Agent, or Firm—Wenderoth, Lind & Ponack

[57] ABSTRACT

To derive spectrum information on chemical intermediates in photochemical reactions during transitional periods, a transient grating spectroscopy uses white light as the probe light in the pico-second region and monochromatic light in the microsecond region. According to the procedure, it is possible to analyze the photochemical reaction of thin films and interface layers as a function of time at a high precision.

6 Claims, 6 Drawing Sheets

TRANSIENT GRATING SPECTROSCOPY

FIELD OF THE INVENTION

The present invention relates to a transient grating spectroscopy. More particularly, the present invention relates to a transient grating spectroscopy and a method for analyzing a chemical reaction which are useful in the analysis of chemical intermediates occurring in the transitional period in a reaction.

PRIOR ART

It is very important in the production of various substances and their application to precisely analyze the reaction over time. Various methods have been offered to analyze chemical reactions. Typical conventional methods include, for example, fluorescence spectroscopy and absorption spectroscopy.

In recent years, the photochemical reaction over time of a thin film and an interface layer whose thickness is on the order of several micrometers or below has been actively studied.

However, the analysis of the reaction of a thin film and an interface layer is very difficult because in a chemical reaction, the number of the existent chemical intermediates in the thin film or interface layer is extremely small.

Such a thin film or interface layer can be analyzed, only when the chemical intermediates give off fluorescence, by using time-resolved fluorescence analysis which uses a time-correlated single grating measurement technique. Photochemical reaction of a thin film or an interface layer of a thickness in the order of several hundred to several tens of nanometers can also be analyzed with the time scale of a picosecond by using time-resolved total reflection fluorescence spectroscopy that utilizes total reflection.

Generally, however, many chemical intermediates are nonfluorescent, and it is widely known that many chemical intermediates inn the form of radicals and ion kinds are not fluorescent. For this reason, reaction of these nonfluorescent intermediates can not be analyzed with a conventional fluorescence spectroscopy.

In the case of the absorption spectroscopy mentioned above, on the other hand, reaction in the transitional period can be analyzed irrespective of whether the chemical intermediates give off fluorescence or not, but the measurement is extremely difficult because of the low sensitivity unless the density of the chemical intermediates is relatively high. The absorption spectroscopy is thus not practical for the measurement of thin film and interface layers.

Conventional techniques thus can not analyze the reaction which occurs in a thin film or an interface layer, and the development of a method allowing the analysis of such a reaction from a new perspective has been much anticipated.

Under these circumstances, a possible method of spectroanalysis of the reaction has been proposed, and researchers are much interested in the proposed method. It is the transient grating spectroscopy proposed by K. A. Nelson, R. Casalengo, R. J. D. Miller, M. D. Fayer, J. Chem. Phys., 77 (1982) 1144, IEEE J. Quantum Electron., Special issue on dynamics gratings and four-wave mixing, QE-22 (1986) ed. by H. J. Eichler (1986).

In this method, as exemplified in FIG. 1, a plurality of exciting radiations are applied simultaneously in the same phase to a sample at the specified area at an angle in order to produce interference fringes at a place where pulses overlap. Various phenomena occur at the crest of the interference fringes, including 1) Photochemical reaction and generation of chemical intermediates,
2) Generation of heat by photochemical reaction and nonradiation transition, and
3) Change in molecular polarization and orientation of molecules due to an electric field of light (electrooptical Kerr effect).

These phenomena give rise to a change in the refractive index of sample, and thus the transient grating fringes (diffraction grating) with variable refractive indexes are produced by the exciting radiation.

Accordingly, when a different probe light is applied to the diffraction grating, that particular probe light is diffracted. Transient diffraction gratings appear and disappear with chemical reactions and thus it is possible to measure the change in reaction as a function of time by detecting the change in the intensity of the diffracted light over time.

With the above transient grating spectroscopy, however, laser light of a single wavelength is used as the probe light, and thus the method has in drawback in that the probe wavelength can be varied only within a very limited range of the laser oscillating wavelength. For this reason, it is extremely difficult, or practically almost impossible, to analyze the spectrum of the chemical intermediates as a function of time.

SUMMARY OF THE INVENTION

The present invention has been made in consideration of the above, and intends to offer a new transient grating spectroscopy by solving the drawbacks of the conventional transient grating spectroscopy while preserving the advantages of said spectroscopy, so that a photochemical reaction of the thin film and interface layers containing nonfluorescent chemical intermediates can be analyzed as a function of time at a high precision.

To solve the above problem, the present invention offers a transient grating spectroscopy for analyzing photochemical reactions, and intends to derive spectrum information on chemical intermediates of a given sample by measuring the intensity of diffracted light of a probe light by irradiating interference fringes by a white probe light, said interference fringes being produced by irradiating the sample by a plurality of exciting radiations simultaneously. Further, the present invention offers a method wherein the probe light is a femto-second white light for the picosecond region, and a monochromatic light or a steady-state white light for the microwave region, and a method wherein the exciting radiation is totally reflected from the interface of a sample.

DETAILED DESCRIPTION OF THE INVENTION

The present invention is different from the conventional transient grating spectroscopy wherein the probe light consists of a laser light of a single wavelength, but allows acquisition of spectrum information on chemical intermediates of thin film and interface layers at a high precision by using a white light as the probe light and by adopting, further, the total reflection condition.

Figure 1:
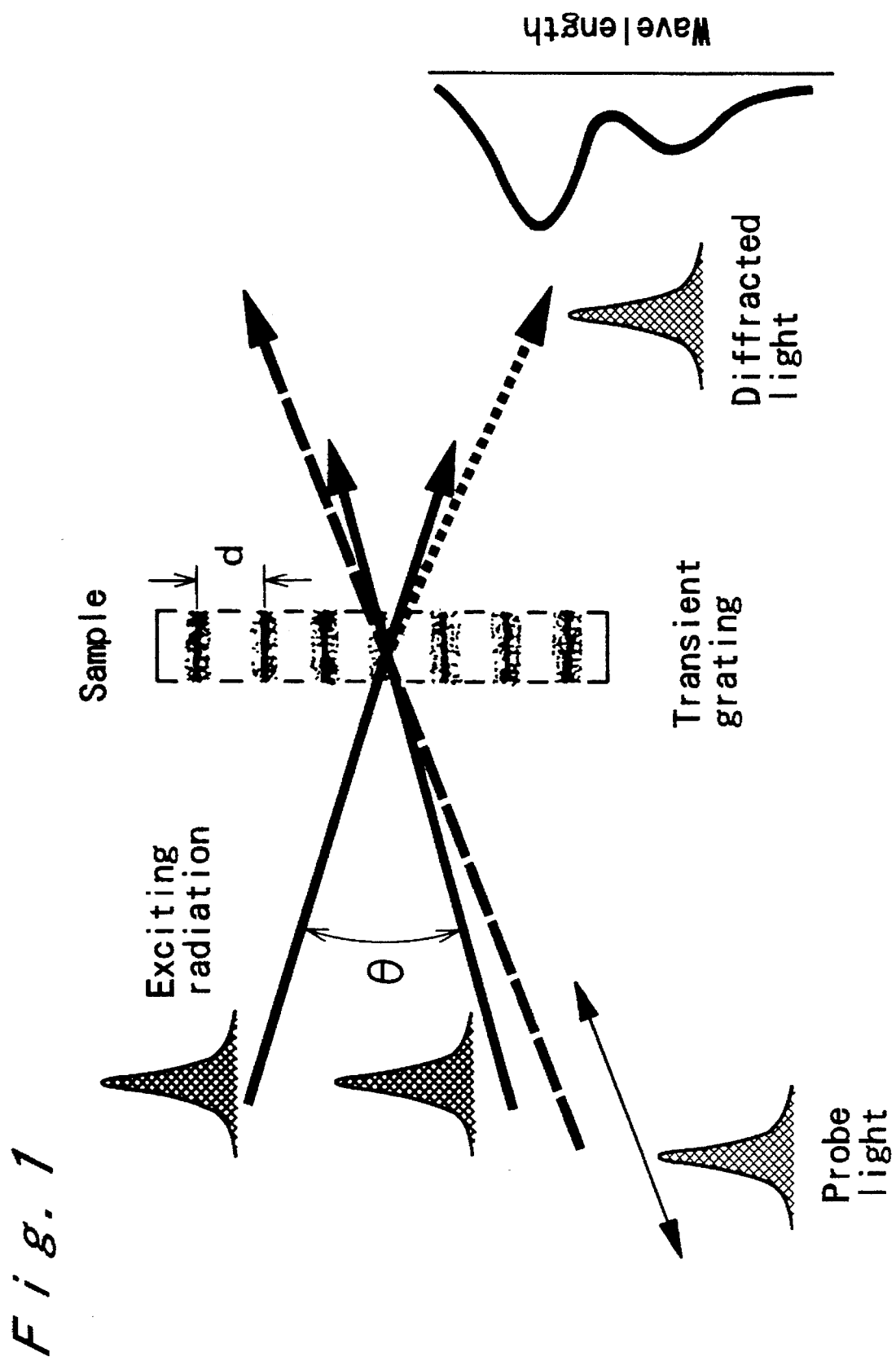
FIG. 1 shows a schematic structural diagram illustrating the principle of the transient grating spectroscopy.
Figure 2:
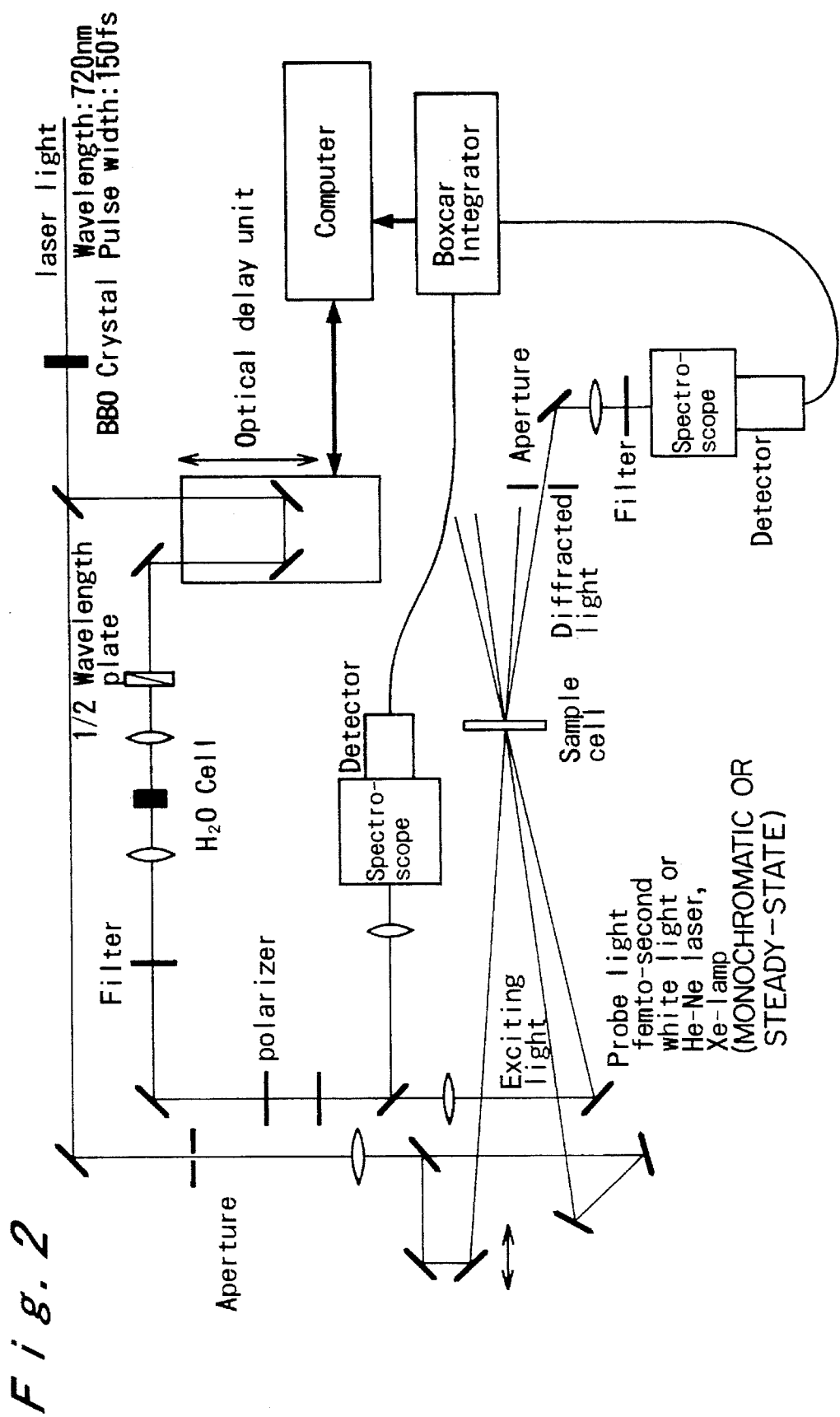
FIG. 2 shows a structural concept diagram illustrating an example of embodiments of the present invention.

FIG. 2 shows an example of the transient grating spectrometric systems which can be used in the present invention.

The laser system, for example, can be a femto-second dye laser which is arranged in a 3-step amplification as exemplified in FIG. 2.

The exciting radiation is split into multiple beam bundles, typically into two, and are applied to the sample cell at a certain angle to generate a transient diffracted grating.

The probe light may be an ordinary He-Ne laser, steady-state Xe lamp, or a femto-second white light which is produced by converging the femto-second laser pulses on water (1 cm cell), said femto-second laser pulses being the leftover after removal of the double wave. The He-Ne laser light or Xe lamp is used for the time-resolved measurement in the several tens of nanoseconds to microseconds region. Diffracted light is separated as it passes through a spectroscope, is detected by a photoelectron multiplier and a digital straight oscilloscope or a multi-channel detector with a gate, and the resultant data are transmitted to a microcomputer. Femto-second white light is used as the probe light for the time-resolved measurement in the pico-second region. Time difference with the pumping light is converter into a difference of distance by an optical delay unit to measure the change in the intensity of diffracted light over time.

In the present invention, further, it is possible to analyze the photochemical reaction of a thin film and interface layers. The method of the present invention is effective for analyzing a reaction of the interface layers ranging from a few hundred to 10 nanometers.

The means that in the present invention, when an exciting radiation is introduced from a sapphire prism of a high refractive index to a sample of a low refractive index, the laser light is totally reflected when the incident angle is equal to or greater than a certain value. This angle is called a critical angle. Even when an exciting radiation is introduced at an angle equal to or greater than the critical angle, resulting in total reflection (illustrated by the double-headed arrow in FIG. 2), the exciting radiation soaks into the sample as evanescent waves by a quantity equivalent to the order of the wavelength. It is thus possible to excite the sample with these evanescent waves.

Now therefore, when a plurality of exciting radiations are emitted under the total reflection condition, the interfered electric field turns out evanescent waves which soak into the sample, with the result that a transient diffraction grating is generated on the interface layer of a thickness in the order of the wavelength. Probe lights are applied to the grating and the change in the strength of the diffracted light is measured as a function of time in order to analyze various reactions occurring on the thin film and interface layers, etc. at a high precision.

The present invention is described in more detail by referring to working examples below.

EXAMPLE 1

A sample of thin film was actually analyzed using the transient grating spectroscopy of the present invention.

The laser system of the spectrometric system consists of a femto-second dye laser which is a 3-step amplifier shown in FIG. 2. The pulse width was 150 fs, and the output was 400 µJ at 720 nm, and approximately 35 µJ at double-waves (360 nm). Sapphire was used in the prism of the sample cell. The probe light consisted of an ordinary He-Ne laser, steady-state Xe lamp, and a femto-second white light which was produced by converging femto-second laser pulses on water (1 cm cell), said femto-second laser pulses being the leftover after removal of the double wave.

The He-Ne laser light and Xe lamp were used for the time-resolved measurement in the several tens of nanoseconds to microseconds region. For the time-resolved measurement in the pico-second region, femto-second white light was used as the probe light.

The sample was an approximately 4 µm thick polystrene film containing 10 wt % benzophenone. The benzophenone/polystyrene film is nonfluorescent, and hence can not be measured with a time-resolved fluorescence analysis method.

Figure 3:
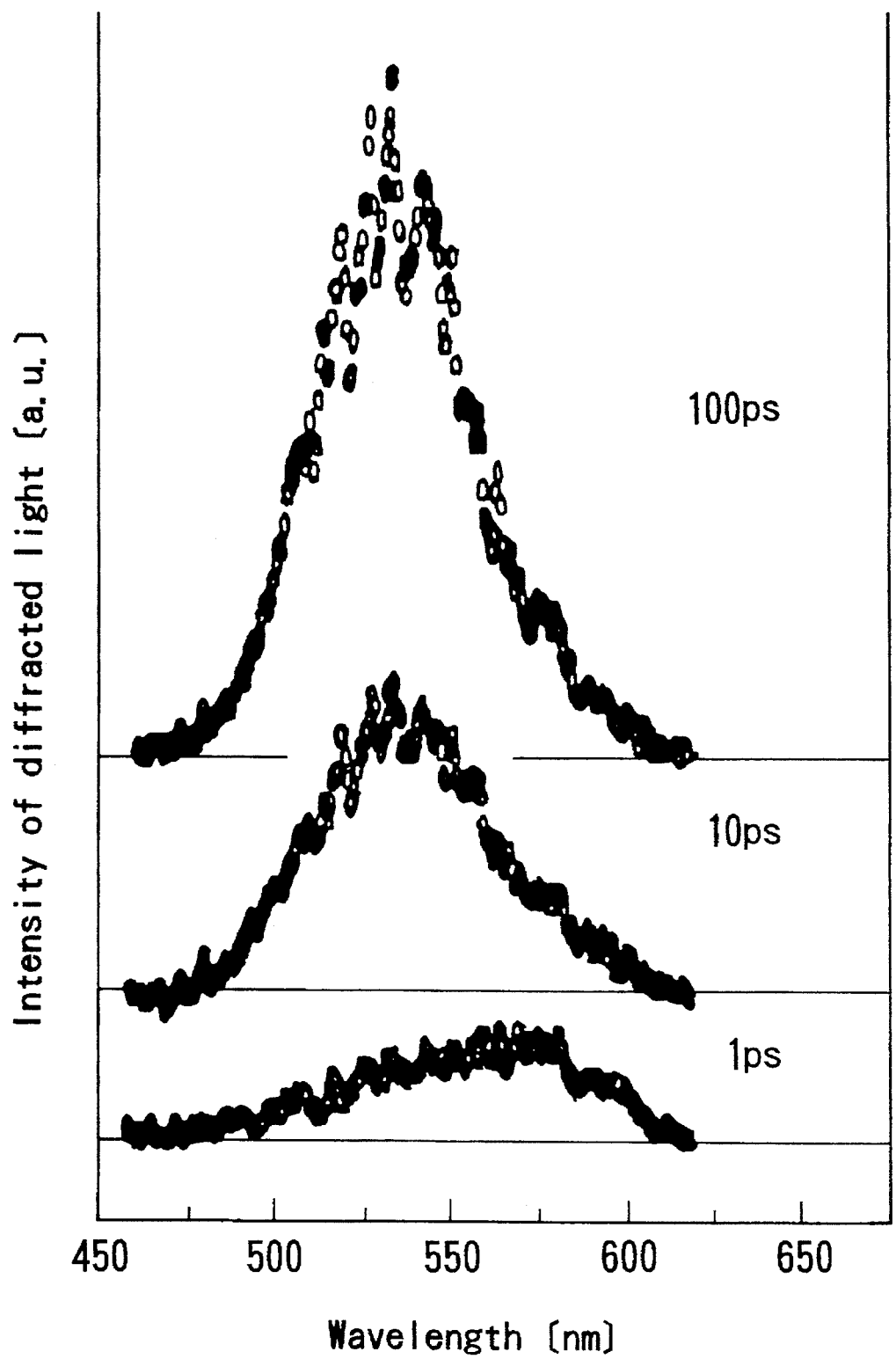
FIG. 3 shows a diagram illustrating the relation between wavelength and intensity of diffracted light as an embodiment of the present invention.

The results of the measurement by the transient grating spectroscopy are shown in FIG. 3.

In the initial stage of 1 ps on the start of excitation, the transient diffraction spectrum has a peak at approximately 575 nm. As time goes on, the peak shifts to about 530 nm. The shift indicates that benzophenone has changed from the excited singlet state to the excited triplet state (intersystem crossing) in the polystyrene film.

Figure 4:
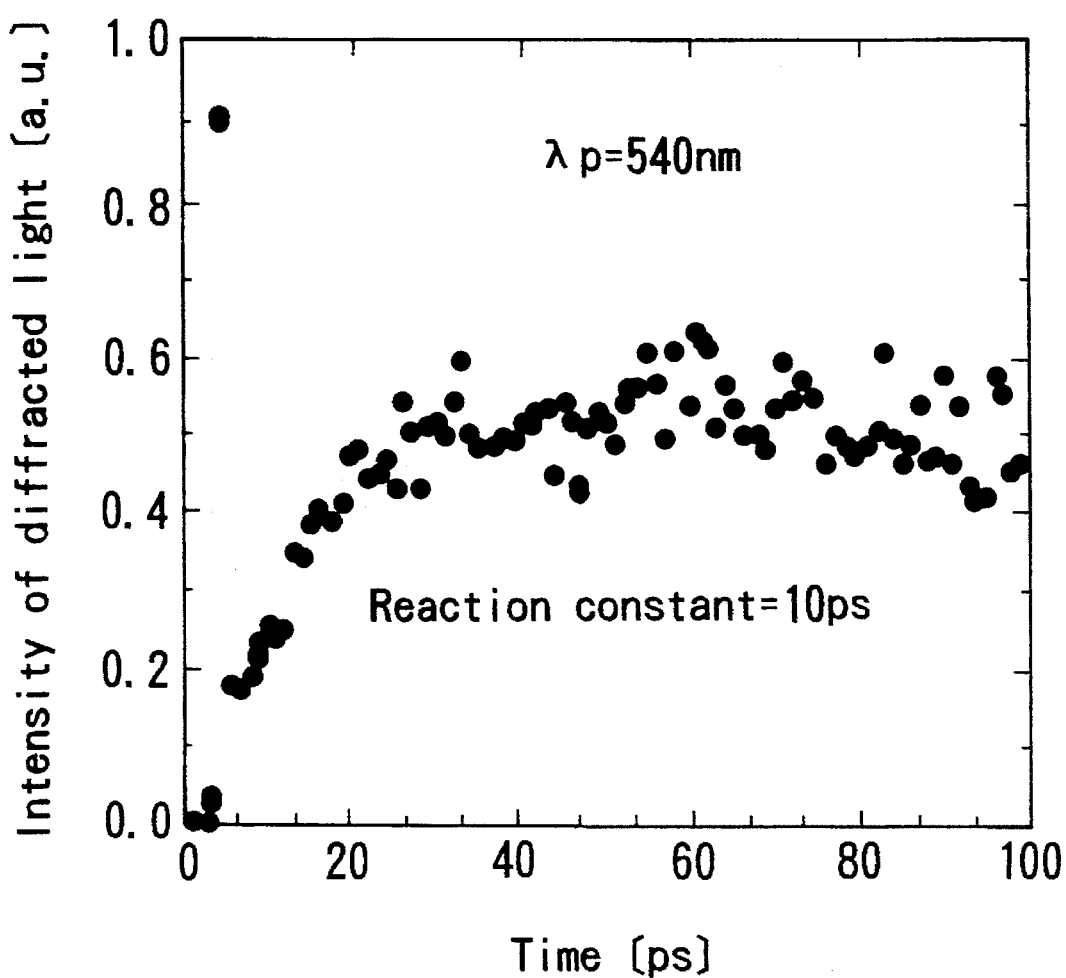
FIG. 4 shows a diagram illustrating the relation between time and intensity of diffracted light as an embodiment of the present invention.

The result of the analysis indicates that the velocity constant of this intersystem crossing was approximately 10 ps as shown in FIG. 4.

Figure 5:
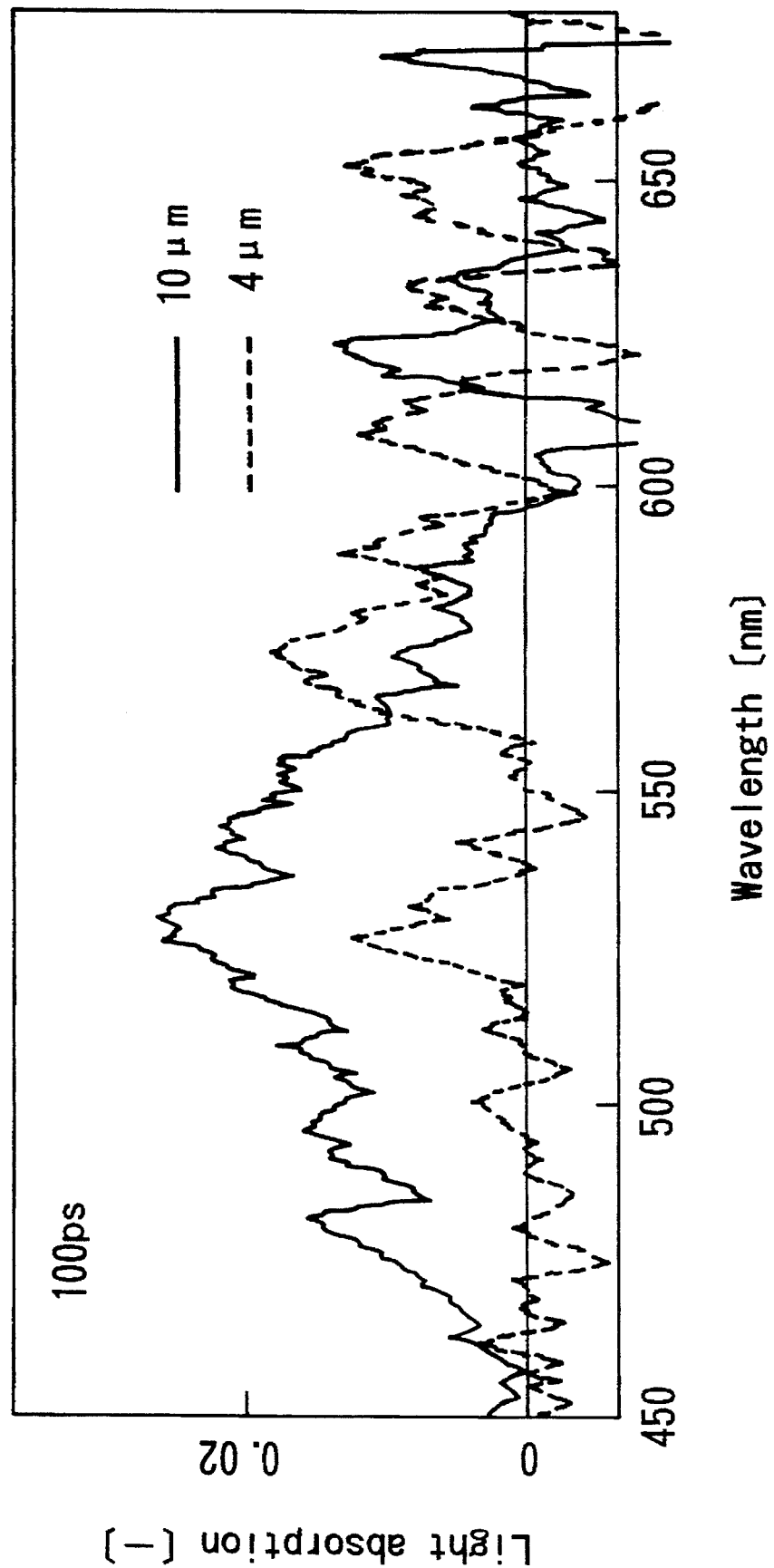
FIG. 5 shows a diagram illustrating the relation between wavelength and absorbance at 100 ps after excitation as compared with FIG. 3.

FIG. 5 shows the transient absorption spectrum at 100 ps on start of excitation of benzophenone/polystrene film measured with the exciting radiation of the same intensity.

As is clear from FIG. 5, concentration of the chemical intermediates in approximately 4 µm thick film was too low for the absorption spectroscopy to measure the transient absorption spectrum.

It has been confirmed, as described above, that the transient grating spectroscopy of the present invention is very effective for the analysis of the reaction of a sample which is too thin to be measured by an ordinary absorption spectroscopy.

EXAMPLE 2

A thin liquid crystal film of 4-cyano-4'-heylbiphenyl was measured in a microsecond region under the total reflection condition using the transient grating spectroscopy of the present invention.

Figure 6:
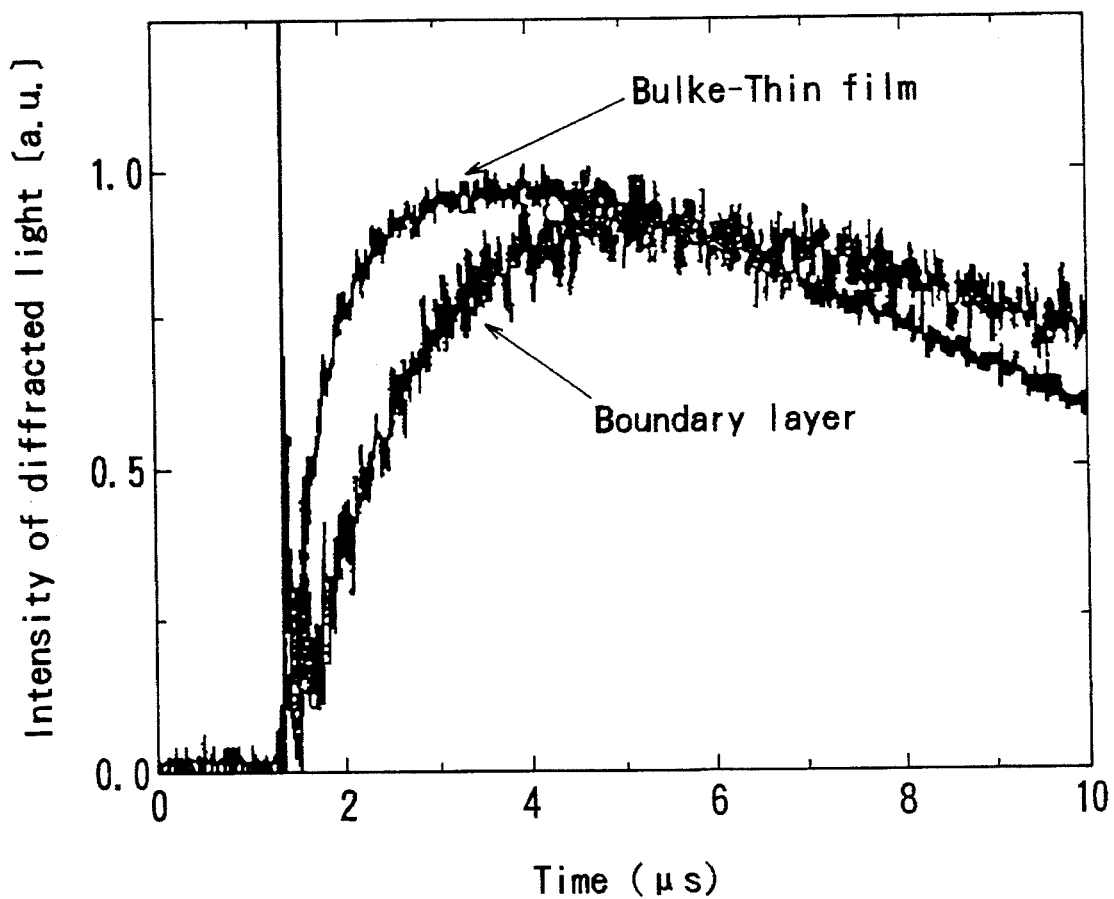
FIG. 6 shows a diagram illustrating the relation between time and the intensity of diffracted light as a working example of the present invention under the condition of total reflection of the exciting radiation.

The result is shown in FIG. 6.

As is clear from FIG. 6, the interface layer (0.2 m thick) obviously rises slower than the bulk film.

In the case of a cyanobiphenyl liquid crystal, the cause of occurrence of diffraction in the microsecond region seems to be either the term of absorption of the excitation triplet state of a relatively long life or the term of the heat generated by non-radiation transition from the excitation triplet state to the ground state. In the He-Ne laser wavelength region, the effect of absorption by the triplet state of the cyanobiphenyl liquid crystal is minimal (a small absorption coefficient), and for this reason, FIG. 6 seems to shown that this measurement relates to the term of the non-radiation transition. This does not conflict with the fact that the signal has a rise.

As described above, the total reflection transient grating spectroscopy of the present invention allows for the analysis of the reaction of the interface layers of submicrometers to several tens of nanometers in thickness.

As described in detail above, the present invention does not rely on the difference of the intensity of light but follows the absolute detection method wherein only the intensity of diffracted light is measured for producing the desired result, so that the S/N ratio is good even for those corresponding to weak absorption, and measurements can be carried out in the high dynamic range. The present invention thus makes it possible to analyze the reaction of a thin film and interface layers over time at a high precision.

We claim:

1. A transient grating spectroscopy method comprising:

irradiating a plurality of excitation radiations simultaneously onto a sample to generate resultant interference fringes;

irradiating a white probe light onto said interference fringes to generate resultant diffracted probe light;

measuring an intensity of said diffracted probe light; and, deriving spectrum information of a chemical intermediate of the sample from said intensity of said diffracted probe light.

2. A method as claimed in claim 1, wherein said white probe light is femto-second white light and said spectrum information is in a pico-second region.

3. A method as claimed in claim 1, wherein said plurality of excitation radiations are totally reflected from an interface of said sample.

4. A method as claimed in claim 1, wherein said plurality of excitation radiations and said white probe light are obtained from a same light source.

5. A method as claimed in claim 2, wherein said plurality of excitation radiations and said white probe light are obtained from a same light source.

6. A method as claimed in claim 3, wherein said plurality of excitation radiations and said white probe light are obtained from a same light source.

* * * * *